United States Patent
Brönnimann et al.

(10) Patent No.: US 10,265,211 B2
(45) Date of Patent: Apr. 23, 2019

(54) IMPLANT

(71) Applicant: OSTOMYCURE AS, Oslo (NO)

(72) Inventors: Benedict Brönnimann, Penthaz (CH); Mats Erik Kindahl Cardell, Sollentuna (SE); Jan Anders Berglund, Järfälla (SE); Robert Axelsson, Gränna (SE)

(73) Assignee: Ostomycure AS, Oslo (NO)

( * ) Notice: Subject to any disclaimer, the term of this patent is extended or adjusted under 35 U.S.C. 154(b) by 707 days.

(21) Appl. No.: 14/774,505

(22) PCT Filed: Mar. 14, 2014

(86) PCT No.: PCT/EP2014/055207
§ 371 (c)(1),
(2) Date: Sep. 10, 2015

(87) PCT Pub. No.: WO2014/140344
PCT Pub. Date: Sep. 18, 2014

(65) Prior Publication Data
US 2016/0030227 A1 Feb. 4, 2016

(30) Foreign Application Priority Data

Mar. 14, 2013 (GB) .................................. 1304649.5

(51) Int. Cl.
*A61F 5/44* (2006.01)
*A61F 5/445* (2006.01)
(Continued)

(52) U.S. Cl.
CPC .............. *A61F 5/445* (2013.01); *A61F 5/449* (2013.01); *A61F 2002/045* (2013.01); *A61F 2002/048* (2013.01); *A61F 2005/4455* (2013.01)

(58) Field of Classification Search
CPC combination set(s) only.
See application file for complete search history.

(56) References Cited

U.S. PATENT DOCUMENTS 3,663,965 A * 5/1972 Lee, Jr. ............. A61M 39/0247
604/175
4,119,100 A * 10/1978 Rickett ................... A61F 5/445
138/93

(Continued)

FOREIGN PATENT DOCUMENTS

EP 0 178 650 A2 4/1986
EP 1 632 201 A1 3/2006
(Continued)

OTHER PUBLICATIONS

Search Report, Russian Appl. No. 20150143680, dated Nov. 27, 2017.
(Continued)

*Primary Examiner* — Tatyana Zalukaeva
*Assistant Examiner* — Guy K Townsend
(74) *Attorney, Agent, or Firm* — Winston & Strawn LLP

(57) ABSTRACT

An implant that has a tubular interior section for implantation into a patient, an exterior section connected to the interior section and an ingrowth member that includes a three-dimensional porous structure. The three-dimensional porous structure is typically located at the inner circumference of the interior section and has desirable properties to facilitate ingrowth of tissue.

18 Claims, 15 Drawing Sheets

(51) Int. Cl.
*A61F 5/449* (2006.01)
*A61F 2/04* (2013.01)

(56) References Cited

U.S. PATENT DOCUMENTS

| | | | | |
|---|---|---|---|---|
| 4,183,357 | A * | 1/1980 | Bentley | A61F 5/445 604/175 |
| 4,217,664 | A * | 8/1980 | Faso | A61F 2/0063 600/32 |
| 4,534,761 | A * | 8/1985 | Raible | A61F 5/445 128/899 |
| 5,098,397 | A * | 3/1992 | Svensson | A61M 39/0247 604/174 |
| 5,234,408 | A * | 8/1993 | Griffith | A61F 5/445 600/30 |
| 5,269,774 | A * | 12/1993 | Gray | A61F 5/445 604/332 |
| 5,290,251 | A | 3/1994 | Griffith | |
| 5,423,761 | A * | 6/1995 | Hein | A61B 1/00137 251/149.2 |
| 5,425,761 | A * | 6/1995 | Lundgren | A61M 39/0247 604/174 |
| 5,882,341 | A * | 3/1999 | Bousquet | A61M 39/0247 128/DIG. 26 |
| 6,017,355 | A * | 1/2000 | Hessel | A61F 5/445 604/174 |
| 6,438,397 | B1 * | 8/2002 | Bosquet | A61B 5/14532 600/310 |
| 7,699,824 | B2 * | 4/2010 | Axelsson | A61F 5/448 604/338 |
| 7,935,096 | B2 * | 5/2011 | Johansson | A61M 25/02 604/175 |
| 8,647,304 | B2 * | 2/2014 | Axelsson | A61F 5/445 604/164.04 |
| 8,821,462 | B2 * | 9/2014 | Axelsson | A61F 5/445 604/332 |
| 8,852,217 | B2 * | 10/2014 | Woodruff | A61M 5/14276 600/37 |
| 9,615,961 | B2 * | 4/2017 | Johansson | A61F 5/445 |
| 2001/0051794 | A1 * | 12/2001 | Bestetti | A61M 39/0247 604/288.04 |
| 2002/0099344 | A1 * | 7/2002 | Hessel | A61F 5/445 604/338 |
| 2004/0006396 | A1 * | 1/2004 | Ricci | A61B 17/68 623/32 |
| 2004/0184876 | A1 * | 9/2004 | Hessel | A61F 5/448 403/326 |
| 2006/0052759 | A1 * | 3/2006 | Johansson | A61M 25/02 604/277 |
| 2007/0244452 | A1 * | 10/2007 | Axelsson | A61F 5/448 604/338 |
| 2009/0192464 | A1 * | 7/2009 | Axelsson | A61F 5/445 604/164.04 |
| 2010/0174255 | A1 * | 7/2010 | Axelsson | A61F 5/448 604/333 |
| 2011/0178540 | A1 * | 7/2011 | Axelsson | A61F 5/445 606/153 |
| 2011/0196324 | A1 * | 8/2011 | Johansson | A61M 25/02 604/338 |
| 2011/0251452 | A1 * | 10/2011 | Villani | A61F 5/445 600/37 |
| 2012/0123361 | A1 * | 5/2012 | Johansson | A61F 5/445 604/337 |
| 2012/0289916 | A1 * | 11/2012 | Johansson | A61M 25/02 604/337 |
| 2014/0052085 | A1 * | 2/2014 | Johansson | A61F 5/445 604/338 |
| 2016/0030227 | A1 * | 2/2016 | Bronnimann | A61F 5/445 604/338 |
| 2016/0045358 | A1 * | 2/2016 | Bronnimann | A61F 5/445 604/339 |
| 2016/0045359 | A1 * | 2/2016 | Bronnimann | A61F 5/445 604/338 |

FOREIGN PATENT DOCUMENTS

| | | |
|---|---|---|
| WO | 92/08499 A1 | 5/1992 |
| WO | 01/08597 A1 | 2/2001 |
| WO | 2007/099500 A1 | 9/2007 |
| WO | 2009/024568 A1 | 2/2009 |
| WO | 2010/125346 A1 | 11/2010 |
| WO | 2011/126724 A1 | 10/2011 |
| WO | 2012/007755 A2 | 1/2012 |
| WO | 2012/131351 A2 | 10/2012 |

OTHER PUBLICATIONS

International Search Report and Written Opinion, PCT/EP2014/055207, dated Jul. 31, 2014.

* cited by examiner

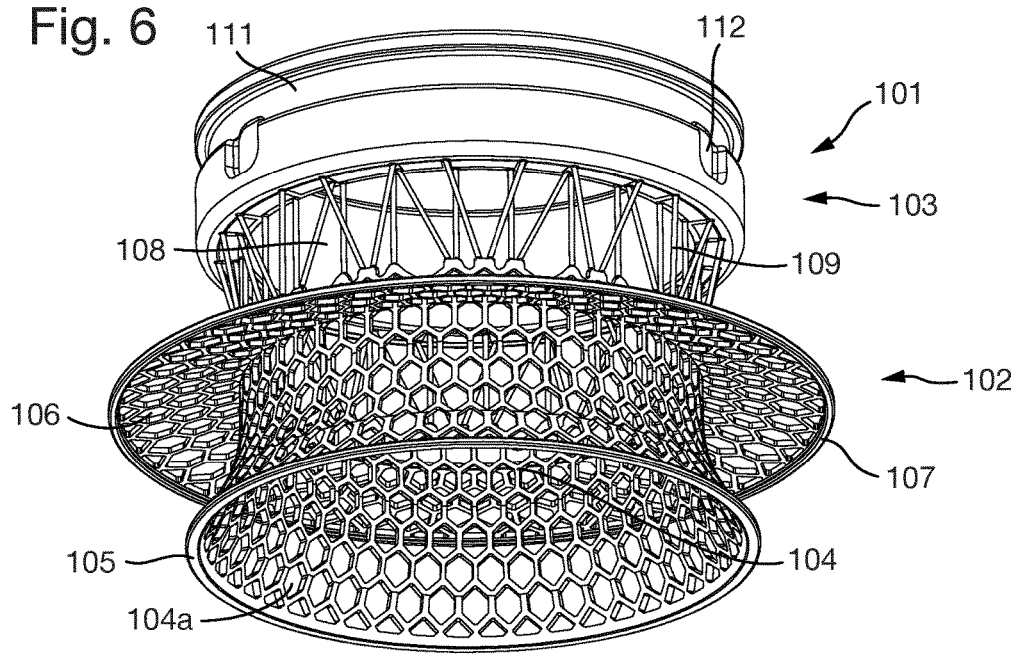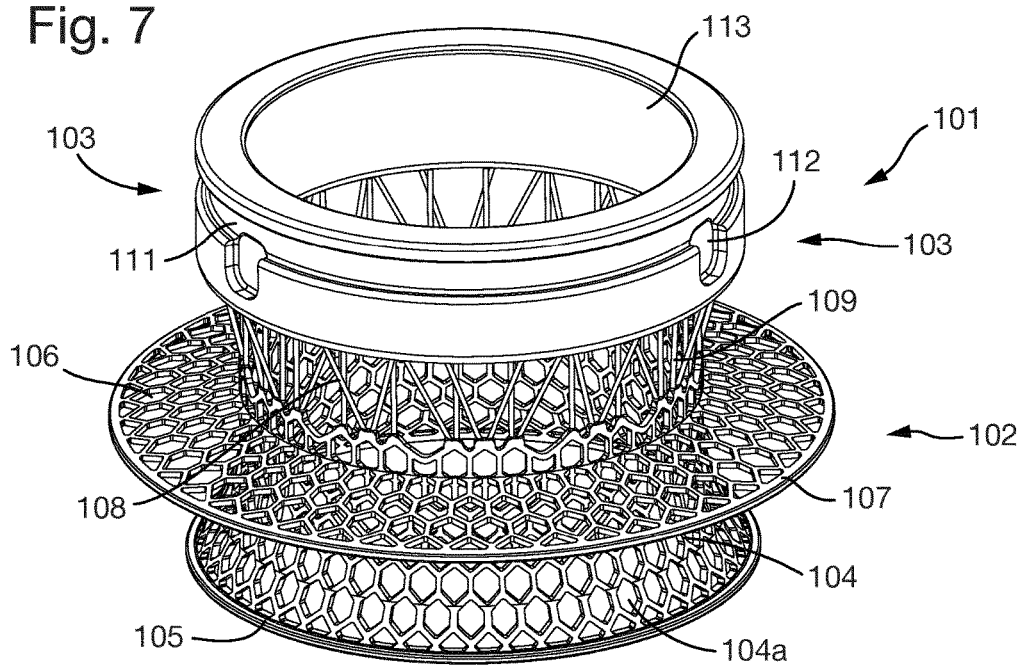

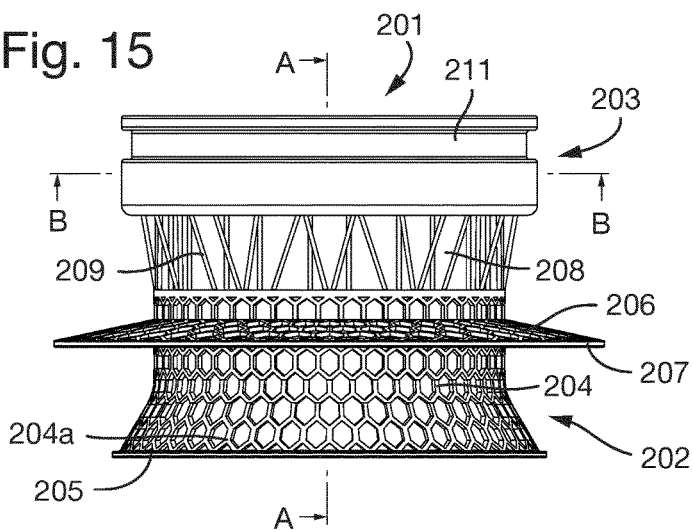
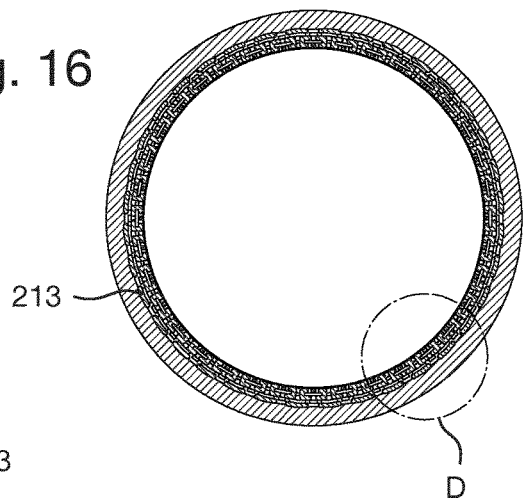
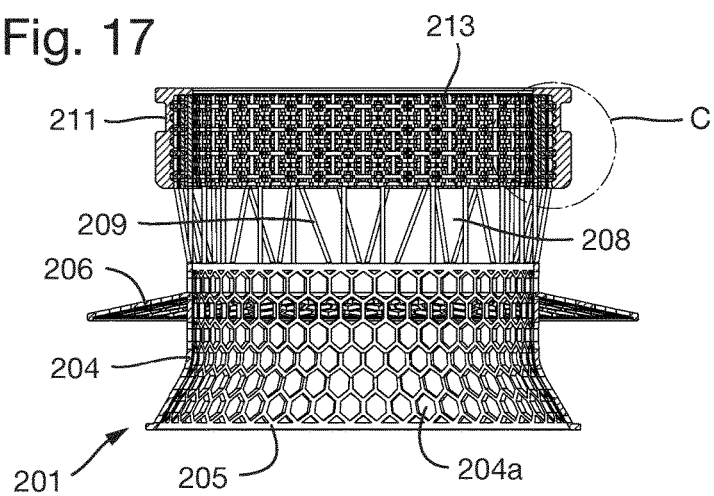

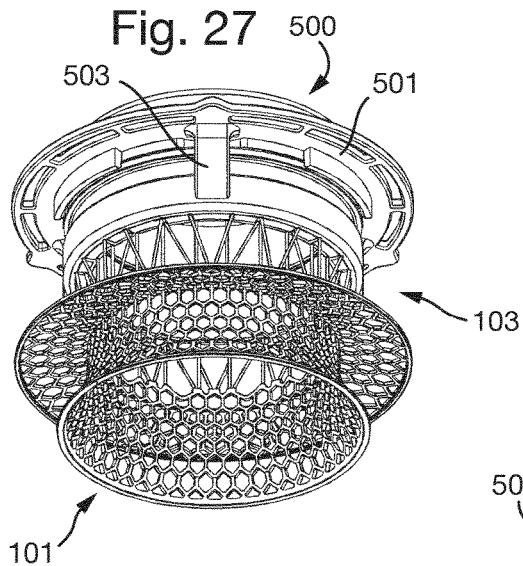
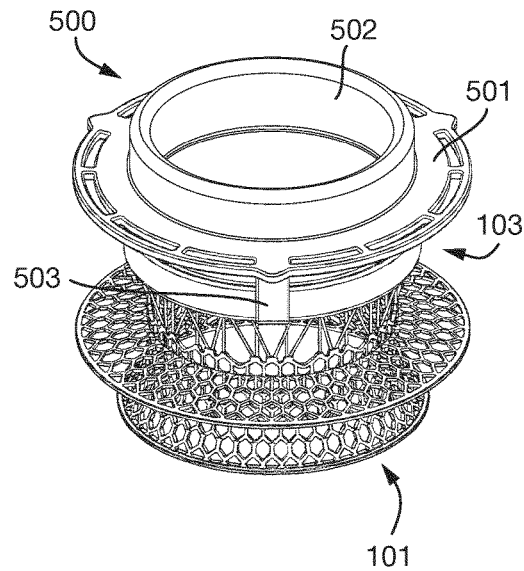
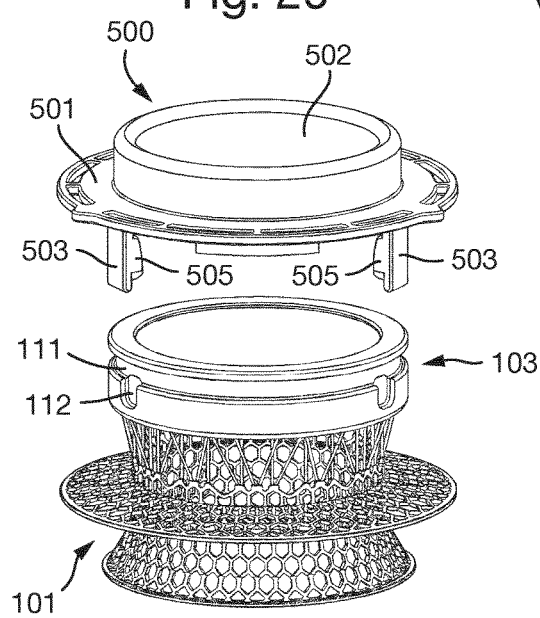

IMPLANT

CROSS-REFERENCE TO RELATED APPLICATIONS

This application is a 371 filing of International patent application no. PCT/EP2014/055207 filed Mar. 14, 2014, which claims the benefit of British application no. 1304649.5 filed Mar. 14, 2013.

BACKGROUND

The present invention relates to an implant, particularly a percutaneous ostomy implant, and a surgical method, which may use that implant, preferably for creating a continent reservoir in communication with a percutaneous port.

Ileostomy and colostomy are common operations which may be necessitated, for example, by malignancy or chronic bowel inflammation. The surgery is called an ileostomy if the colon and rectum are removed and a colostomy if the rectum alone is removed. Similarly an abdominal urostomy is created when the urinary bladder has to be removed due to, for example, bladder cancer. In these operations, a stoma is formed in the abdominal wall to which a bowel segment is connected.

Ostomy is a generic term for any such procedure where a stoma is created.

The stoma, in most cases, has to be connected to a bag for the collection of bodily waste. However, instead of a conventional ileostomy, it is possible to make a reservoir known as a "Kock pouch" from the distal part of the ileum. The pouch is formed in such a way that a nipple valve is created which serves to close the reservoir, whilst allowing it to be drained intermittently by means of a catheter. This is an example of a so-called continent ileostomy (CI) and it was formerly an attractive alternative to conventional ileostomy but is now rarely used. The complexity of the procedure and the high potential for complications—most of them related to dysfunction of the continence nipple valve—has deterred many surgeons from adopting the operation today.

The ileopouch anal anastomosis (IPAA) is today the gold standard worldwide for these patients but, as with a CI, this operation is also risky and failures are common, mostly leading to pouch excision with loss of bowel. Conversion of a failed IPAA to a CI would be a preferable option but, again, surgeons are reluctant to perform this complex and unreliable technique. Likewise, conversion of a malfunctional orthotopic neobladder or Bricker urostomy would be desirable.

In its earlier patent application EP 1632201 A1, the present applicant disclosed a percutaneous ostomy implant comprising a solid-walled cylindrical body and an anchoring section in the form of a circular flange. The device was designed to be implanted through the abdominal wall and secured by an anchoring section located below the fascia, above the muscle layer. This section comprised inner and outer concentric rings interconnected by S-shaped members in order to provide an axially resilient structure which could absorb shear stresses and consequently reduce the risk of tissue damage. Spaces around the S-shaped members and the provision of numerous apertures in the rings allowed for tissue ingrowth and vascularization. It was proposed to connect the device to the side of the bowel wall and by providing a removable lid on the cylindrical body a continent ostomy could be provided.

U.S. Pat. No. 6,017,355 discloses another solid-walled implant. This was provided with a fabric coating comprising Dacron velour which was intended to encourage tissue ingrowth.

A development of this implant was disclosed in WO 2007/099500 in which the solid-walled cylindrical body was replaced by an axially outer tubular part spaced from the anchoring section by circumferentially-spaced legs. The tubular part penetrated the skin and formed a ring for connection to a bag or lid. This implant was designed to receive a bowel section drawn up through it; the spaces between the legs allowed the generation of a tissue bond between the inner part of the abdominal wall and the serosal tissue of the bowel in order to provide a more secure, stable, leak-proof and well-vascularized tissue-implant junction. In some embodiments, a circumferential ingrowth mesh was additionally provided. This extended along most of the length of the tubular part with an annular gap being provided between it and the tubular part to facilitate growth of serosal tissue through the mesh.

In a further development, disclosed in WO 2009/024568, the present applicant proposed a cylindrical body formed of two axially-spaced tubular parts. The outer tubular part penetrated the skin and provided a connecting ring. The inner tubular part was attached to an anchoring flange of the type previously described. The two parts were connected together by a "distance means" comprising either radially-spaced legs or a rigid cylindrical ingrowth mesh which allowed for the generation of a tissue bond between the abdominal wall and the bowel. By means of this arrangement, a break was provided in the possible infection path along the implant from the skin.

In a still further development, the applicant disclosed in WO 2010/125346 a percutaneous ostomy implant comprising a cylindrical part for mounting an external detachable device, a cylindrical ingrowth mesh and a circular flange for anchoring the implant. The cylindrical part and circular flange were attached to opposite ends of the ingrowth mesh, with the mesh extending inside the cylindrical part. The implant was configured such that when it is implanted in the abdominal wall of a patient, abdominal tissue including the epidermis meets the ingrowth mesh and is able to attach therethrough directly to serosal tissue of a bowel segment inside the implant. Thus, it was based on the hypothesis that by allowing the epidermis to attach directly to the serosal tissue, bacterial infection (i.e. bacterial attachment to implant surface and subsequent migration) can be prevented.

However, whilst this implant was found to be effective in ensuring sound attachment of the serosal tissue to the abdominal tissue, it had a drawback in that it became more difficult to ensure a fluid-tight seal between the exterior parts of the implant and the bowel segment. This was because the implant relied upon the bowel segment extending within the cylindrical part and maintaining secure infiltration of serosal tissue through the mesh inside that part to form a good seal to the implant. If the bowel receded below the cylindrical part, a leakage path could be formed through the mesh, even if the bowel segment and abdominal wall remained integrated and the implant remained secure and free of infection.

WO 2011/126724 discloses a stoma stabilising device intended to prevent stomas from constricting over time and hence requiring surgical re-opening. The preferred embodiments comprise a flexible mesh tube with a radially extending mesh anchoring flange. In some variants, multiple layers of mesh may be employed.

In WO 2012/131351, the applicant presented further developments relating to percutaneous ostomy implants comprising a connecting member, a first tubular ingrowth member and a second tubular ingrowth member radially outwardly spaced from the first tubular ingrowth member, a radially-extending dermal anchor to engage the abdominal wall beneath the dermis, and/or a tubular ingrowth member arranged around the connecting member. This implant was formed by a laser cutting process.

However, in trials, this implant was still found to have problems. For example, this implant was fixed to the muscle sheath with an anchor provided at the bottom. This was not ideal with patients adding or losing weight since the implant height was fixed and the thickness of a patient's abdomen could vary over time. There was also insufficient ingrowth at the top of the implant. These factors could lead to skin problems, implant overgrowth, excessive implant protrusion and leakage from the system.

SUMMARY OF THE INVENTION

According to one aspect of the invention, there is provided an implant comprising a tubular interior section for implantation into a patient and an exterior section connected to the interior section, a surface of the exterior section comprising a three-dimensional porous structure at an inner circumference thereof. By providing a three-dimensional porous structure at an inner surface of the exterior section, this provides a ingrowth means into which tissue can grow. By providing a three-dimensional structure, this can provide better and more secure ingrowth than previously used two-dimensional ingrowth means. A three-dimensional ingrowth porous structure can provide a "skeleton" structure for tissue ingrowth and creates a physiological need that promotes cellular ingrowth into the structure. Accordingly, in one claimed aspect of the invention, the porous structure is rigid. Furthermore, by providing the three-dimensional porous structure at the exterior section, this can lead to more ingrowth at the outer end of the implant, making it more secure at the exterior end and reducing the possibility of leakage from the system.

Preferably, there is no gap between the three-dimensional porous structure and the rest of the exterior section.

The porous structure is preferably connected to the rest of the exterior section at least at first and second end regions thereof, and/or preferably at a number of points over the height of the porous structure.

Preferably, the porous structure extends to an exterior end (top) of the exterior section. In this way, a bowel segment, for example, may be secured by ingrowth right up to the top end of the implant, thereby providing a more secure implantation of the implant and also reducing the likelihood of leakage. Alternatively, the porous structure may extend to within 1 mm, 2 mm or 3 mm of the exterior end (top) of the exterior section.

The implant may be, for example, an ostomy implant, such as a percutaneous ostomy implant, which is suitable for implantation into the abdominal wall of a patient.

The tubular interior section may be substantially cylindrical but may be of generally any form with an opening along a longitudinal axis thereof. The opening should ideally be large enough for a bowel segment to pass therethrough.

The shape and/or size (e.g. the internal and/or external diameter) of the cross-section of the interior section may vary along its length.

The exterior section may be generally ring-shaped, tubular or cylindrical, for example.

The exterior and/or interior sections may have a substantially circular cross-section.

The exterior section is ideally coaxial with the interior section.

The exterior section may have an outer diameter (measured from its outer edges) of 10-60 mm, more preferably 25-35 mm or 25-30 mm.

The exterior section may have an inner diameter (measured from its inner edges) of 5-55 mm, more preferably 15-30 mm or 20-25 mm.

The interior section may have an inner diameter (measured from its inner edges) at its narrowest point of 5-55 mm, more preferably 15-30 mm or 20-25 mm.

Implants whose exterior and interior sections have a smaller inner diameter (i.e. towards the lower ends of the scales mentioned above) may be particularly useful for urostomies. Implants whose exterior and interior sections have a larger inner diameter (i.e. towards the upper ends of the scales mentioned above) may be particularly useful for colostomies.

The interior and exterior sections may have circular cross-sections or any other shape. Thus, since the cross-sections of these sections need not necessarily be circular, references to "diameter" above refer to the maximum distance measured perpendicularly across the sections.

Preferably, the interior and exterior sections have the same cross-section (e.g. in size and/or shape), at least at the point where the sections meet.

The porous structure is preferably arranged around the entire inner circumference of the exterior section. Alternatively, the porous structure may be provided around at least 70%, at least 75%, at least 80%, at least 85%, at least 90%, at least 95%, at least 97%, at least 98% or at least 99% of the inner circumference of the exterior section. By providing all, or at least a significant part of the inner circumference of the exterior section with a porous structure, this ensures that ingrowth means is provided around all, or at least a significant part, of the inner circumference of the exterior section so secure and sufficient ingrowth may be obtained.

The porous structure preferably has a thickness (or a minimum thickness) of at least 0.5 mm, at least 0.6 mm, at least 0.7 mm, at least 0.8 mm, at least 0.9 mm, at least 1.0 mm, at least 1.1 mm, at least 1.2 mm, or at least 1.25 mm. In preferred embodiments, the porous structure has a thickness of around 1.25 mm or 1.75 mm. By providing a porous structure of at least 0.5 mm (or greater) thick, this means that the porous structure may be formed of a number of layers (e.g. two or three layers) and helps to ensure secure ingrowth into the porous structure. The thickness of the porous structure may be measured in a radial direction with respect to the longitudinal axis of the implant.

The porous structure should ideally also be thin enough that there is enough space inside the exterior section for a bowel segment to pass through it. Thus, preferably the porous structure has a thickness of 3.0 mm or less, 2.5 mm or less, or 2.0 mm or less. The thickness of the porous structure may be in a range of 0.5 to 2.0 mm, 2.5 mm, or 3.0 mm, for example.

Preferably, the porous structure is completely permeable and has no dead ends. For example, each passage entering the porous structure ideally also has an exit. Alternatively, at least 80%, at least 85%, at least 90%, at least 95%, or at least 97% of the openings into the porous structure have a corresponding exit. This can provide the most secure ingrowth into the ingrowth means.

The thickness of any member forming the porous structure is preferably less than or equal to 500 µm, less than or equal to 450 µm, less than or equal to 400 µm, less than or equal to 350 µm, or less than or equal to 300 µm. The thickness of any member forming the porous structure is preferably greater than or equal to 100 µm, greater than or equal to 125 µm, greater than or equal to 150 µm, or greater than or equal to 200 µm. By providing a porous structure formed of members with such dimensions, this means that the porous structure has dimensions which are biologically comfortable (mimicking coral, for example), thereby creating a physiological need which promotes secure ingrowth of tissue into the porous structure.

For similar reasons, preferably, the maximum diameter of any opening in the porous structure is 500 µm, 450 µm, 400 µm, 350 µm, 300 µm, 250 µm, 200 µm or 150 µm. The minimum diameter of any opening in the porous structure may be 50 µm, 75 µm, 100 µm or 125 µm, for example. The diameters of any openings (or of at least 70%, 75%, 80%, 85%, 90% or 95% of the openings) in the porous structure are preferably in a range of 100 to 400 µm, more preferably, 150 to 350 µm, more preferably 250 to 350 µm, more preferably 275 to 325 µm.

The cross-sections of any members and/or openings in the porous structure may be circular or any other regular or irregular shape such as elliptical, super-elliptical, quadratic with rounded corners, hexagonal, octagonal, polygonal, polygonal with rounded corners, or rectangular with rounded corners, for example. Thus, since the cross-sections of the members and/or openings forming the porous structure need not necessarily be circular, references to "diameter" above refer to the maximum distance measured perpendicularly across a member and/or an opening in the porous structure.

In further optimized embodiments, both the members forming the porous structure and the openings of the porous structure may vary independently in size and/or shape within one porous structure, in a random or structured (regular) pattern.

The porous structure preferably has a height of at least 3 mm, at least 4 mm, at least 5 mm, or at least 6 mm, where the height is the length of the porous structure measured in a direction parallel to the longitudinal axis of the implant.

The porous structure preferably has a height of less than 10 mm, less than 8 mm, less than 8 mm or less than 7 mm.

Preferably, the height of the porous structure is in a range from 3 to 9 mm, more preferably from 4 to 8 mm, more preferably from 5 to 7 mm, more preferably from 6 to 7 mm.

In a preferred embodiment, the height of the porous structure is 6.35 mm.

The porous structure has a height that is ideally great enough to provide a sufficiently large ingrowth zone, but also small enough that there is limited implant protrusion above skin level (the porous structure being ideally located within the exterior section).

However, in some embodiments the porous structure may extend into the interior section and/or a further porous structure (for example with any of the features discussed in relation to the first porous structure) may be provided in the interior section. Thus, a porous structure with a height of up to around 40 mm may be provided. Such a porous structure could extend from the exterior section into the interior section.

The porous structure may be flexible, semi-flexible or rigid.

The porous structure is preferably integral with the rest of the exterior section. This means that the exterior section, at least, can be formed as a single element (for example with the rest of the implant as well) and there is no need to attach a porous structure inside the exterior section.

The porous structure is preferably made from a biologically acceptable material such as titanium. This helps to prevent patients reacting adversely to the implant. Preferably, a commercially pure titanium is used such as medical grade 2 titanium. Examples of other materials that could be used include titanium grades according to ASTM F67 (ISO 5832) medical grade 1, 2, 3, 4 or 5, specifically grade 5 Ti64ELI, other biocompatible metals and alloys such as Elgiloy, or a chrome-cobalt-molybdene alloy, biocompatible ceramics and biocompatible polymers.

The porous structure may be formed from interconnecting members. The members may be arranged in layers (e.g. concentric layers), for example. The layers could be connected by connecting members. Accordingly, the connecting members will typically have a radial extent. These are preferably two to four layers, but more preferably three.

The members may form a regular, repeating pattern throughout the porous structure. For example, the porous structure could be formed from a plurality of repeating units.

Alternatively, the porous structure may have an irregular or partly irregular structure.

In either case it will be appreciated that the porous structure is typically porous in multiple directions (i.e. passages through the structure extend in multiple directions) so that a coral-like structure is provided. This is in contradistinction from conventional mesh which is essentially two-dimensional, with porosity (and passageways) extending in only one direction, relative to the surface of the mesh.

Preferably, the exterior section comprises engagement means (e.g. a engagement mechanism) for engaging with a device. For example, the exterior section may comprise one or more grooves, recesses or indentations into which corresponding attachment means provided on a lid or other device may be attached. Preferably, the engagement means are located on an exterior surface of the implant, or at the very top of the inner surface of the implant, so that tissue inside the implant is not affected when a device is attached to the implant.

Alternative engagement means include: a threaded interface for screwing a device onto the implant, a bayonet attachment, a magnetic interface (i.e. one or more magnets arranged on the implant), a rubber or rubber-like material encompassing the outer perimeter, or like a cork in the inner diameter, for example, of the implant.

In some embodiments, at an inner end, the interior section may comprise a radially extending part, for example in a cone or trumpet-like shape. This can help to secure the implant in a patient's body as it can resist forces acting on the implant in more directions.

Alternatively or additionally, the implant may comprise an anchoring flange extending radially outwardly from the interior section. This can also help to secure the implant in a patient's body.

The anchoring flange may extend to a greater radius than the radially extending part (if both such components are provided).

The anchoring flange may extend perpendicularly from the implant. However, it is preferred that it extends at an angle of less than 90° such that it is sloping towards the interior end of the implant. The anchoring flange may be curved. These features can allow the anchoring flange to follow the general curvature of a patient's body, reducing the likelihood of damage or problems caused by its implantation.

The anchoring flange may be formed of or comprise an ingrowth means (e.g. an ingrowth part) such as a mesh, e.g.

a hexagonal mesh. Such an ingrowth means can allow body tissue to grow into the flange and secure the implant in the body.

The interior section preferably extends longitudinally inwardly (i.e. downwardly as shown in the figures) from a point at which the anchoring flange is connected to it. The interior section may additionally or alternatively extend longitudinally outwardly (i.e. upwardly as shown in the figures) from a point at which the anchoring flange is connected to it.

The implant may be flexible, semi-flexible or rigid. In some embodiments the flexibility/rigidity of the implant may vary over its structure. For example, the interior section may be more flexible than the exterior section so that, for example, the interior section is more adapted to the surrounding tissue, but the exterior section is still sufficiently rigid that a lid may be attached to it. This may be achieved by using different materials in different sections of the implant, for example. Such different materials could be joined with welds, glue, friction, threads, or other techniques.

The interior section may be formed of or comprise an ingrowth means (e.g. an ingrowth part) such as a mesh, e.g. a hexagonal mesh. Such an ingrowth means can allow body tissue to grow into the interior section and secure the implant in the body.

The interior section may comprise a plurality of rods, the rods having a diameter of less than or equal to a biologically comfortable length such as 500 μm, 450 μm, 400 μm, 350 μm, 300 μm, 250 μm or 200 μm. The diameter of the rods is preferably similar to the average diameter of human skin hairs, e.g. 20 to 200 μm. By forming the interior section, or part of the interior section, from such thin components, the amount of material used to form the implant can be minimised, thereby reducing the likelihood of a patient reacting adversely to the implant. Furthermore, since the rods have a diameter of less than or equal to a biologically comfortable length, this reduces the possibility of the patient's body rejecting or reacting adversely to the implant.

This concept is considered to be inventive in its own right, thus, according to a second aspect of the invention, there is provided an implant comprising a tubular interior section for implantation into a patient and an exterior section connected to the interior section, wherein the interior section comprises a plurality of rods and the rods have diameters of less than or equal to 500 μm, less than or equal to 450 μm, less than or equal to 400 μm, less than or equal to 350 μm, less than or equal to 300 μm, less than or equal to 250 μm or less than or equal to 200 μm. The diameters of the rods may be in a range of 100 to 400 μm, 100 to 300 μm, 150 to 250 μm, 100 to 200 μm, 200 to 300 μm, or 250 to 300 μm, for example.

Preferably, the rods have a diameter of greater than or equal to 20 μm, greater than or equal to 50 μm, greater than or equal to 75 μm, or greater than or equal to 100 μm. In a preferred embodiment, the rods have a diameter of 275 μm.

The rods may have a circular cross-section or any other shape. Thus, since the cross-sections of the rods need not necessarily be circular, references to "diameter" above refer to the maximum distance measured perpendicularly across a rod.

The rods are preferably arranged circumferentially around the implant. At least some of the rods may be parallel to the longitudinal axis of the implant, for example.

Depending on the diameter of the rods and the material from which they are made, ideally sufficient rods should be provided to make the implant strong enough to withstand pulling forces acting on it, with a safety margin, for example. The stronger the material used for forming the rods, the smaller the number of rods required. Ideally, the smallest number of rods possible are used to keep the amount of material used to a minimum.

More than 10, 20, 30, 40, 50 or 60 rods may be provided and/or fewer than 150, 140, 130, 120, 110, 100, or 90 rods may be provided.

Preferably, 5 to 150, 20 to 130, 40 to 110, 50 to 100, or 60 to 90 rods are provided.

One or more of the rods is preferably slanted with respect to the longitudinal axis of the implant. This can help to improve the mechanical strength of the implant since such rods can help to withstand torque, shearing and compressing forces acting on the implant. For example, the one or more slanting rods may be arranged at an angle of up to 45°, up to 40°, up to 35°, up to 30°, up to 25°, up to 20°, up to 15° or up to 10° with respect to a longitudinal axis of the implant. Preferably, the one or more slanting rods may be arranged at an angle of at least 5°. In preferred embodiments, one or more slanting rods are arranged at angles of up to 25°.

Rods may be slanted radially inwardly or outwardly from the longitudinal axis of the implant and/or circumferentially or sideways around the implant. The inward or outward radial slant of the rods is preferably less than the circumferential slant. For example, rods may be slanted radially outwards or inwards by an angle of around 15° or less, and/or rods may be slanted circumferentially by an angle of around 25° or less. Rods may be slanted circumferentially in clockwise and/or anti-clockwise directions (when view from the top or exterior end of the implant).

One or more of the rods is preferably parallel with respect to the longitudinal axis of the implant. Such parallel rods can help to withstand axial forces acting on the implant along its longitudinal axis, for example.

Around 30-40%, 30-50%, 40-60%, 50-70% or more of the rods may be slanting.

Around 30-40%, 30-50%, 40-60%, 50-70% or more of the rods may be parallel.

One or more rods may have at least one end located radially inwardly with respect to the implant compared to one or more other rods. Such an arrangement can improve the mechanical strength of the implant, particularly with respect to shear forces. Shear forces may act on an implant, for example, when a patient rises from a chair and contacts a table with the implant, moves sideways and contacts a door-post, or similar situations.

The inner ends of the rods (i.e. the ends of the rods located furthest from the exterior section of the implant) are preferably all located at the same radius of the implant.

The exterior ends of the rods (i.e. the ends of the rods located closest to the exterior section of the implant) may be located at different radii, for example at two or three different radii. In a preferred embodiment, the exterior ends of the rods are located on three imaginary concentric circles. Preferably, the concentric circles are equally spaced.

The radial distance between the radially innermost exterior ends and the radially outermost exterior ends may correspond to the thickness of the porous structure. For example, the radial distance between the radially innermost exterior ends and the radially outermost exterior ends may be around 1.0 to 2.0 mm or 2.5 mm.

Such arrangements of the rods can result in a very rigid, box-like overall structure, which can help to increase the mechanical strength of the implant and distribute the forces acting on the exterior section of the implant more uniformly into the porous structure.

The rods are ideally long enough that, in use, they can extend through the skin (i.e. the epidermis and the dermis) and also ideally extend partially into the hypodermis. For example, the rods may be at least 1.5 mm, at least 2 mm, at least 2.5 mm, at least 3.0 mm, at least 3.5 mm, at least 4.5 mm or at least 5.0 mm long. The rods may have a maximum length of 8.0 mm, 7.5 mm, 7.0 mm, 6.5 mm, 6.0 mm, 5.5 mm or 5.0 mm. In a preferred embodiment, the rods are around 4.8 mm long. Of course, the slanting rods may be slightly longer than the parallel rods. The lengths referred to in this paragraph may refer to the slanting or the parallel rods.

The interior section may comprise an inner interior section part and an outer interior section part.

The outer interior section part preferably comprises the plurality of rods.

The plurality of rods may connect the inner interior section part to the exterior section.

Preferably, the inner interior section part is connected to the exterior section solely by the plurality of rods. This helps to minimise the amount of material used in the implant.

For similar reasons, the outer interior section part is preferably formed solely from the plurality of rods.

The inner interior section part preferably comprises or is formed of an ingrowth means (e.g. an ingrowth part), preferably in the form of a mesh such as a hexagonal mesh. By providing such an inner interior section part, this can help the implant to be implanted securely into a patient's body.

Various optional features of the aspects described above are considered to be independently inventive.

Thus, according to another aspect of the invention, there is provided an implant comprising an ingrowth means in the form of a three-dimensional porous structure, wherein the porous structure has a thickness of at least 0.5 mm. For example, the porous structure could have a thickness of at least 0.5 mm, at least 0.6 mm, at least 0.7 mm, at least 0.8 mm, at least 0.9 mm, at least 1.0 mm, at least 1.1 mm, at least 1.2 mm, or at least 1.25 mm. In preferred embodiments, the porous structure has a thickness of around 1.25 mm or 1.75 mm. As discussed above, by providing an ingrowth means of at least 0.5 mm thick, this ensures that secure ingrowth into the porous structure can be achieved.

According to another aspect of the invention, there is provided an implant comprising an ingrowth means in the form of a three-dimensional porous structure, wherein the porous structure is completely permeable and has no dead ends.

Preferably, each passage entering the porous structure also has an exit.

According to another aspect of the invention, there is provided an implant comprising an ingrowth means in the form of a three-dimensional porous structure, wherein at least 80%, at least 85%, at least 90%, at least 95%, or at least 97% of the openings into the porous structure have a corresponding exit.

According to another aspect of the invention, there is provided an implant comprising an ingrowth means in the form of a three-dimensional porous structure, wherein the thickness of any member forming the porous structure is less than or equal to 500 µm, less than or equal to 450 µm, less than or equal to 400 µm, less than or equal to 350 µm, or less than or equal to 300 µm.

According to another aspect of the invention, there is provided an implant comprising an ingrowth means in the form of a three-dimensional porous structure, wherein the maximum diameter of any opening in the porous structure is 500 µm, 450 µm, 400 µm, 350 µm, or 300 µm.

The implants of any of the above aspects may be a percutaneous ostomy implant, for example. The implants may comprise a tubular interior section and/or a tubular or ring-shaped exterior section. The interior and exterior sections are preferably co-axial. The ingrowth means may be located in the interior and/or exterior section. Preferably, the ingrowth means extends around the circumference of the interior and/or exterior section.

After an implant has been implanted into a patient, it is important that a bowel segment, for example, or other vessel passing through the implant, is secured so that it can grow into the implant.

There are various ways in which the bowel segment, for example, may be secured or fixated. One conventional method is a surgical procedure referred to as a "turnbull". During this procedure, on a conventional stoma the efferent part of the intestine is wrung inside out and attached to the skin surrounding the stoma. However, after this procedure, the stoma often retracts at skin level, leaving a space and resulting in leakage. Also, it is not possible to perform a conventional turnbull with the implant of the above aspects because this would completely cover and hide the implant. It would then not be possible to use a stabiliser device (to hold the implant in position) during healing and it would also not be possible to monitor the healing and ingrowth of the implant. The risk of bodily waste being caught under the turnbull and around the implant would be great, potentially causing infection, and it would not be possible to clean and wash away such trapped waste. In previous processes with an ostomy implant, the intestine was simply left outside the implant or arranged into a "loose hanging turnbull", not connected to anything, and not secured or fixed.

There is therefore a need for providing a way of securing the bowel segment, for example, to provide a more stable environment for the stoma to heal after an ostomy is performed on a patient.

According to a further aspect of the invention, there is provided an adaptor for securing a bowel segment outside a patient's body after an ostomy has been performed, the adaptor comprising: attachment means (e.g. an implant attachment part) for attaching the adaptor to an implant; and securing means (e.g. a bowel segment securing part) to which a bowel segment may be attached.

By providing such an adaptor, a turnbull procedure may be facilitated and the bowel segment can be secured whilst it heals, thereby reducing the likelihood of it retracting during this process. In addition, when used with an implant according to one of the aspects of the invention described above, the bowel segment can be secured close to the porous ingrowth structure (where this is provided in the exterior section of the implant), which further helps to keep the bowel segment in a fixed position, and thereby provides an optimal peaceful healing situation free from significant movements or mechanical stress.

The adaptor may be referred to as a turnbull adaptor.

The implant itself may also be secured with a stabiliser device to hold it in place during healing.

The adaptor should ideally be easy to attach to the implant with the correct alignment.

Preferably, the attachment means are arranged to prevent the adaptor from moving rotationally, horizontally and vertically with respect to the implant, when the adaptor is attached to the implant. This helps to prevent rotational or other forces acting on the vessel during healing.

Preferably, the attachment means are arranged to attach to an outer surface of the implant, for example in a groove, recess or indentation on an outer surface of the implant. The attachment means may be arranged to engage with one or more corresponding grooves, recesses or indentations on the implant.

In a preferred embodiment, the attachment means comprises one or more resilient members. This is a simple way of allowing the adaptor to be attached to an implant. The one or more resilient members may comprise engagement means (e.g. implant engagement parts), such as protruding parts, for engaging with the implant, for example in one or more corresponding recesses on the implant.

Alternative attachment means could also be used. For example, longer or shorter resilient members could be used with corresponding grooves, recesses or indentations, for example, in a correspondingly lower of higher position on the implant. Different shaped protruding parts could also be used. Other alternatives include: a threaded interface for screwing the adaptor onto the implant, a bayonet attachment, a magnetic interface (i.e. one or more corresponding pairs of magnets on the adaptor and the implant), a rubber or rubber-like material encompassing the outer perimeter of the implant and/or an inner perimeter of the adaptor using only friction forces, a rubber or rubber-like material with a ring-like suction-cup on the adaptor for attaching to a polished top surface, for example, of the implant.

The adaptor preferably has an aperture through which the bowel segment may pass. For example, the adaptor may be substantially ring-shaped. Preferably the aperture has the same shape and/or diameter as the inner shape and/or diameter of the corresponding implant. For example, the adaptor may be substantially ring-shaped or tubular. The aperture may have a diameter of 5-55 mm, more preferably 15-30 mm or 20-25 mm.

The securing means may comprise one or more openings in the adaptor through which sutures may be attached. For example, the adaptor may comprise one or more radially extending parts in which the one or more openings are provided. The securing means could alternatively comprise one of more hooks to which sutures may be attached.

The adaptor is preferably made of a plastics material such as a medical quality polyamide. Alternatively, the adaptor may be made of medical grade POM, PEEK, or other similar polymer, a semi-rigid or flexible medical grade polymer such as Mediprene or similar, or titanium or other metal or alloy, depending on the attachment mechanism and manufacturing method.

In some embodiments, a biologically degradable material is used to form the adaptor. The adaptor would then "disappear" automatically after a suitable time, as it is dissolved by the surrounding tissue. Such an adaptor could be made of a medical grade polymer such as PGA poly(glycolide), PDO poly(p-dioxanone), LPLG poly(L-lactide-co-glycolide), DLPLG poly(DL-lactide-co-glycolide) or PHB-PHV copolymer (polyhydroxybutyrate-polyhydroxyvalerate), for example.

Different polymers or other materials will degrade at different rates within the body and therefore a polymer or other material should ideally be used which has a suitable release/degradation rate. For example, a material which could form an adaptor that would degrade after a few weeks (e.g. 2-8 or 5-7 weeks) may be suitable. Such an adaptor would remain in the body long enough for the healing process to take place. Also, factors such as mechanical properties, processing properties, possible sterilisation methods, cost and availability of the material, etc. should be considered when selecting a suitable material. The adaptor is preferably arranged to receive the bowel segment therethrough and allow the bowel segment to be reverted back over the adaptor.

According to a further aspect of the invention, there is provided a kit comprising an implant and an adaptor for securing a bowel segment outside a patient's body after an ostomy has been performed, the adaptor comprising: attachment means for attaching the adaptor to the implant; and securing means to which a bowel segment may be attached.

The kit is preferably sterile.

The adaptor in the kit may be as described in relation to the adaptor aspect of the invention or any of its preferred features above.

The implant in the kit may be as described in relation to any of the implant aspects of the invention or any of their preferred features above.

The present invention also extends to a method of performing an ostomy comprising the use of an implant and/or adaptor as described above.

Thus, according to a further aspect there is provided a method of performing an ostomy comprising providing an ostomy implant according to any aspect or any preferred form thereof as described above; providing a suitable opening for the implant in the body of a patient; implanting the implant in the opening and drawing a bowel segment into the implant to provide a stoma. The method is most preferably as described in more detail below.

Viewed from a further aspect, the invention provides a method of performing an ostomy comprising: implanting a percutaneous ostomy implant according to any aspect or any preferred form thereof as described above in the abdomen; drawing a section of vessel (e.g. bowel) into the implant; and securing it to form a stoma. The implant and/or method are preferably as set out herein.

The implant is preferably used or provided in combination with a lid to prevent leakage and/or to protect the stoma. However, it may also be used in combination with a bag or an evacuation device. Thus, viewed from a still further aspect the invention provides an ostomy implant according to any aspect or preferred from described herein, in combination with a mating lid, bag or evacuation device. Mating is typically by means of a part of the lid, bag or evacuation device having a part that in use engages with the exterior section of the implant and preferably connects thereto by means of an engagement means, such as a circumferential groove around the circumference of the exterior section of the implant. However, it is possible for engagement to be wholly or partially with an internal surface of the exterior section.

The invention also extends to a method of performing an ostomy comprising providing an ostomy implant, which is preferably (but not necessarily) according to any aspect or any preferred form thereof as described above; implanting the implant in an opening in the body of a patient; drawing a bowel segment into the implant to provide a stoma; providing an adaptor according to any aspect or any preferred form thereof as described above at an exterior end of the implant; reverting an efferent end of the bowel segment over the adaptor; and securing the efferent end of the bowel segment. The efferent end of the bowel segment may be secured with sutures, for example. The efferent end of the bowl segment is preferably secured to the adaptor.

Preferably, the adaptor is removably attached to the exterior end of the implant, for example with attachment means such as one or more clips.

After a few weeks, for example, when the intestine has grown enough into the implant, the adaptor may be removed.

In order to remove the adaptor, preferably the part of the intestine protruding outside the implant, which has now started to wizen, for example, is cut away. The adaptor may then be removed. The intestine should then reside permanently just at the top of the implant.

The invention also extends to a method of manufacturing an implant, the implant being according to any of the aspects described above. Preferably, the implant is integrally formed. Alternatively, the implant may be made in parts which are subsequently joined together. The parts may be formed from the same material or two or more different materials.

The implant may be formed by a 3D printing process, for example. Preferably, an electron beam or a laser 3D printing process is used. Alternatively, the implant, or parts thereof, may be moulded or conventionally machined and laser or water-jet cut, or produced by etching and/or punching methods.

The method may comprise polishing at least part of the implant (particularly the exterior section, or the outer surface thereof). This can give a smooth finish.

Any of the aspects of the invention described above may comprise any of the features of the other aspects of the invention, even if not specifically stated.

BRIEF DESCRIPTION OF THE DRAWINGS

Preferred embodiments of the invention will now be described by way of example only and with reference to the accompanying drawings, in which:

FIG. 6 is a perspective view of another embodiment of an implant;

FIG. 7 is another perspective view of the implant of FIG. 6;

FIG. 15 is a side view of the implant of FIG. 13;

FIG. 16 is a cross-sectional view of an implant along the line B-B in FIG. 15;

FIG. 17 is a cross-sectional view of an implant along the line A-A in FIG. 15;

FIG. 27 is a bottom perspective view of the adapter of FIGS. 26(a)-(f) attached to the implant of FIG. 6;

FIG. 28 is a top perspective view of the adapter of FIGS. 26(a)-(f) attached to the implant of FIG. 6; and FIG. 29 is a perspective view of the adapter of FIGS. 26(a)-(f) and the implant of FIG. 6 before attachment.

DETAILED DESCRIPTION OF THE INVENTION

Figure 1:
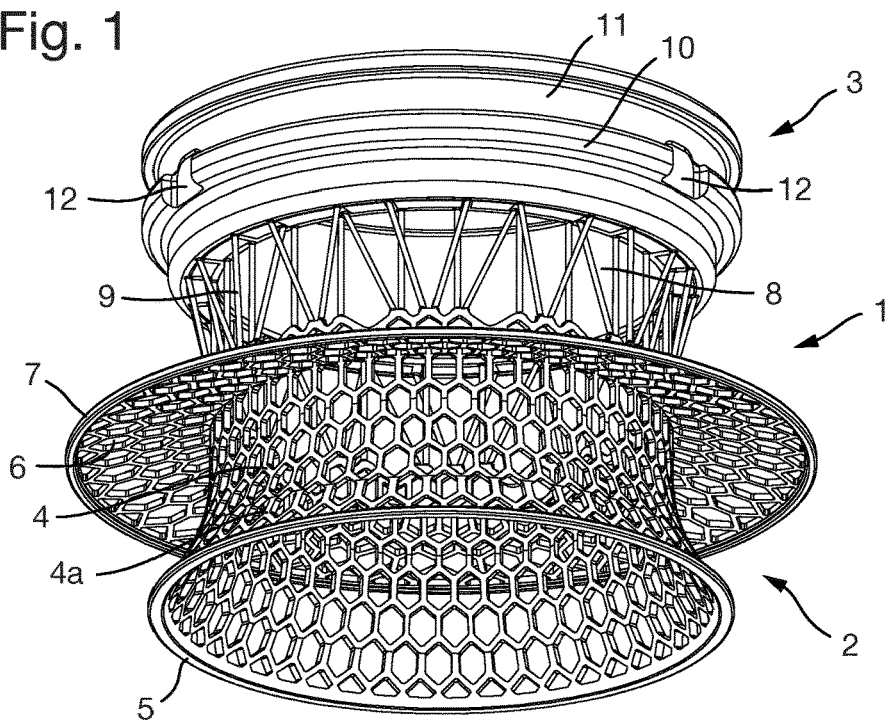
FIG. 1 is a perspective view of an embodiment of an implant.
Figure 2:
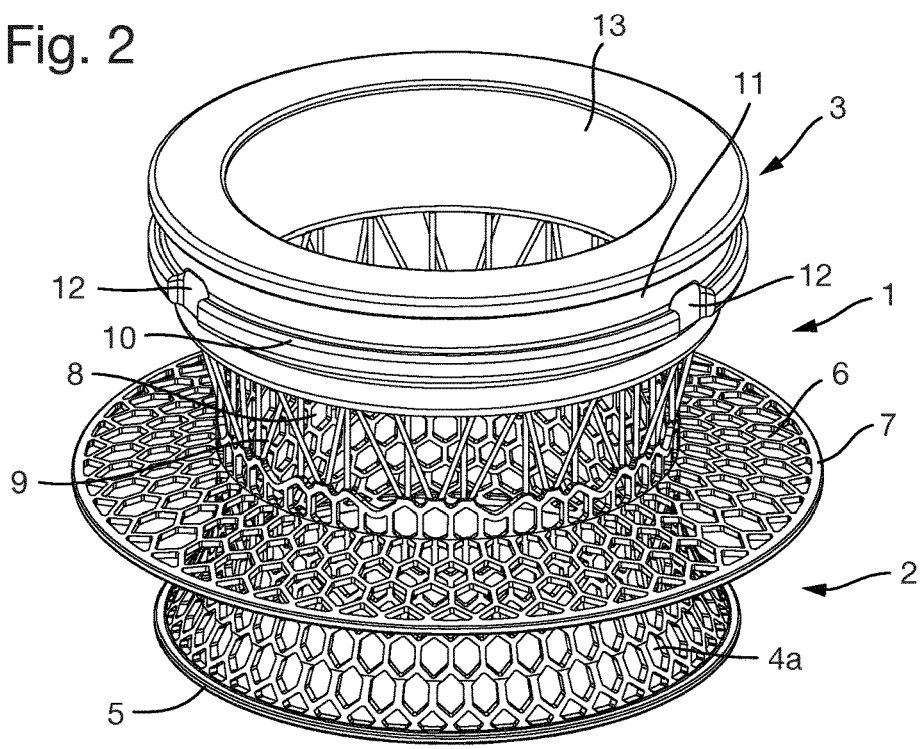
FIG. 2 is another perspective view of the implant of FIG. 1.
Figure 3:
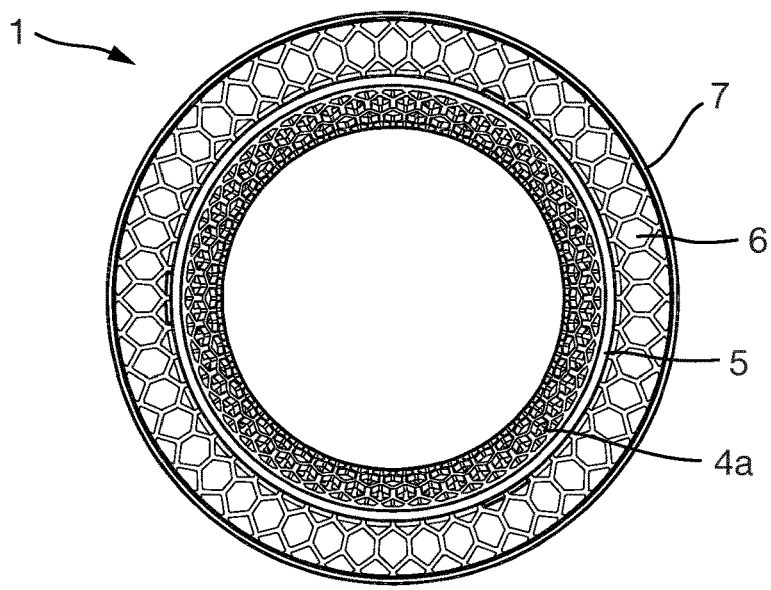
FIG. 3 is a bottom view of the implant of FIG. 1.
Figure 5:
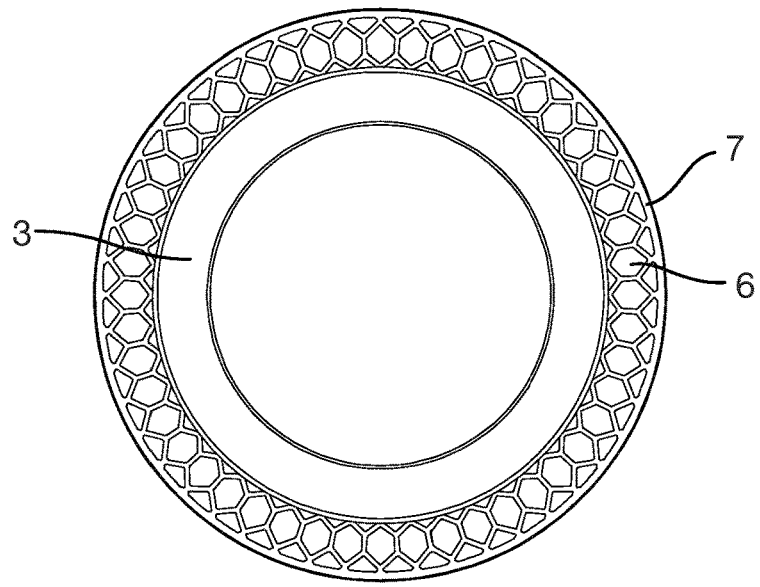
FIG. 5 is a top view of the implant of FIG. 1.
Figure 4A:
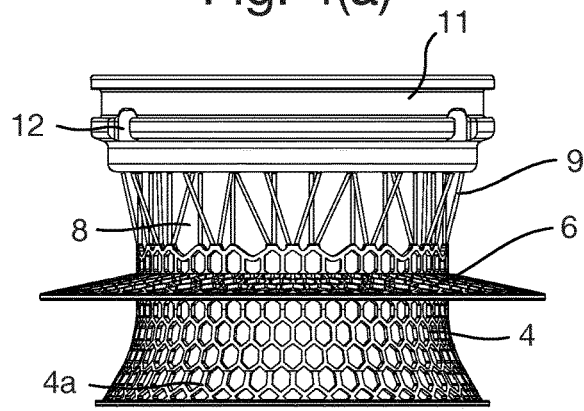
FIGS. 4(a)-(c) are side views of the implant of FIG. 1.
Figure 4B:
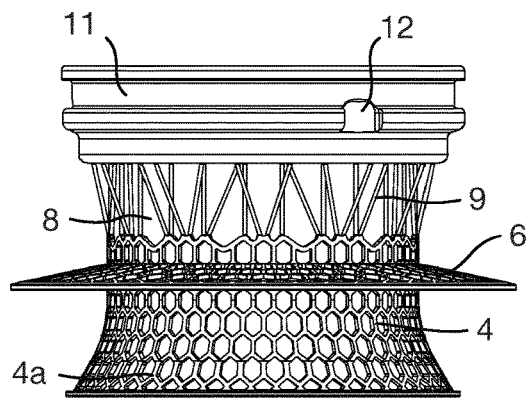
Figure 4C:
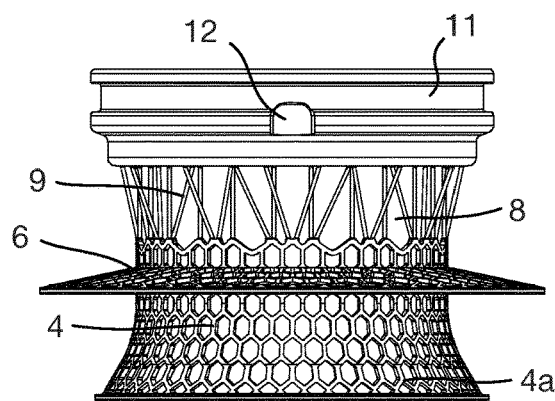
Figure 8:
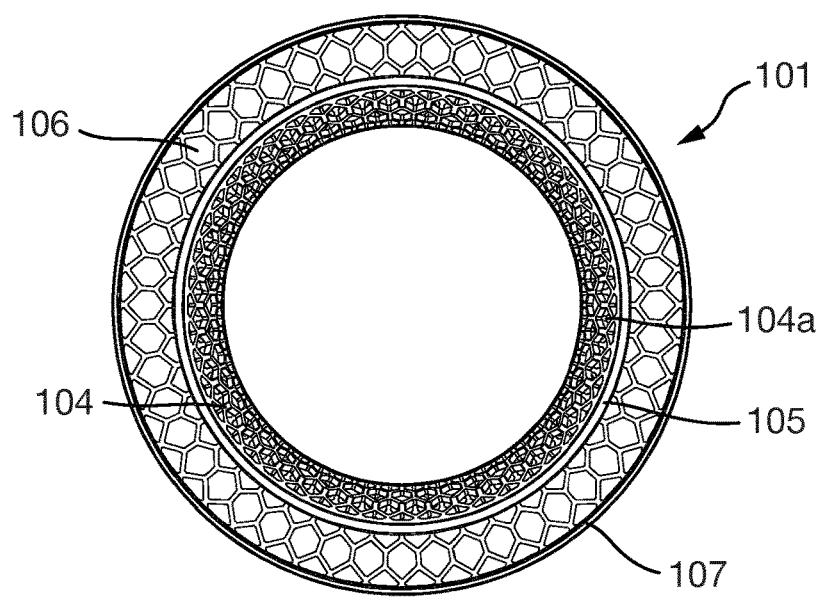
FIG. 8 is a bottom view of the implant of FIG. 6.
Figure 10:
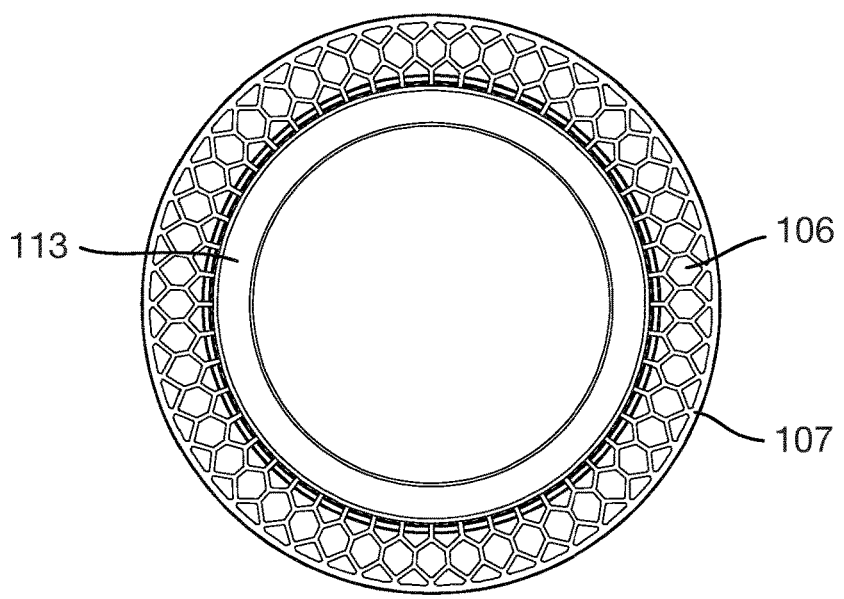
FIG. 10 is a top view of the implant of FIG. 6.
Figure 9A:
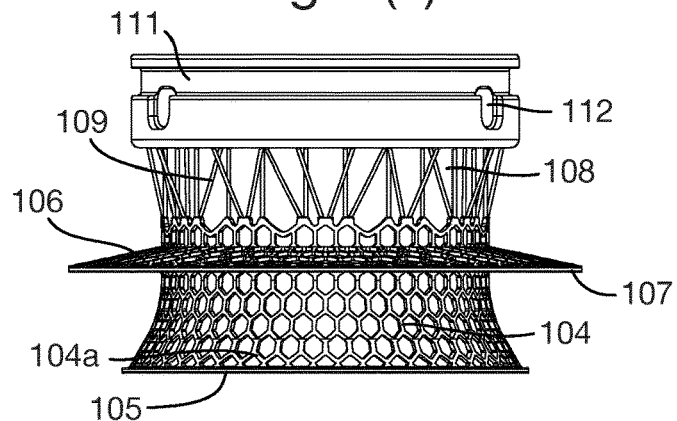
FIGS. 9(a)-(c) are side views of the implant of FIG. 6.
Figure 9B:
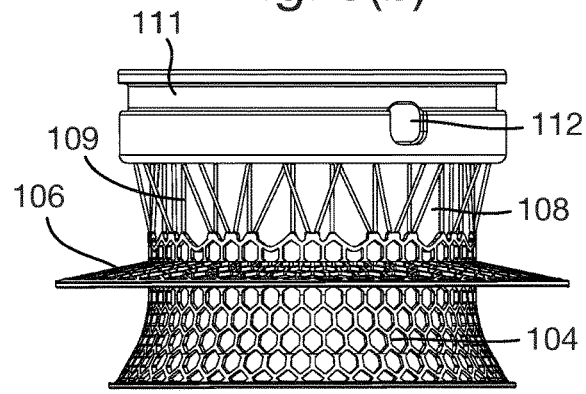
Figure 9C:
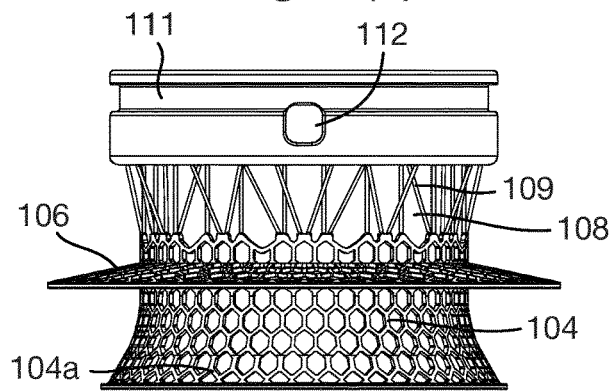

FIGS. 1 to 5 show an embodiment of an implant 1.

The implant 1 is formed of an interior section 2 and an exterior section 3. When implanted in a patient, the interior section 2 is located mostly or entirely inside the patient whereas the exterior section 3 is located mostly or entirely outside of the patient.

The interior section 1 is formed of an inner interior section part 4 and an outer interior section part 8.

The inner interior section part 4 is a substantially cylindrical structure formed of an hexagonal mesh. At its lower (as shown in the figures) or inner end, the cylinder flares radially outwardly in a radially extending part 4a and is terminated by a continuous solid ring 5.

An anchoring flange 6 extends radially outwardly from the inner interior section part 4. This is also made of an hexagonal mesh. The anchoring flange 6 has at its radially outer edge a continuous solid ring 7. The inner interior section part 4 extends both above and below (i.e. outwardly and inwardly from) the anchoring flange 6.

The anchoring flange 6 extends to a greater radius than the radially extending part 4a.

The outer interior section part 8 connects the inner interior section part 4 to the exterior section 3. The outer interior section part 8 is formed from a number of rods 9 extending between the inner interior section part 4 and the exterior section 3. The rods 9 are arranged circumferentially around the implant 1.

Some of the rods 9 are slanted with respect to the longitudinal axis of the implant 1 and others are parallel with it. The slanted rods are angled so that they can withstand rotational forces acting on the implant 1. The rods which are parallel with the longitudinal axis of the implant 1 are for withstanding loads acting on the implant 1 longitudinally.

Some of the rods 9 have an exterior end which is located radially inwardly compared to the exterior ends of other rods 9. The interior ends of the rods 9 are all located at the same radius of the implant 1.

The rods 9 have a maximum diameter of 300 μm and a length of around 4.8 mm. The slanting rods are slightly longer than the parallel rods.

The exterior section 3 is ring-shaped and has an outer circumferential groove 11 to which part of a lid or a connector (e.g. to a bag or other device) or other device may be attached.

The exterior section 3 also has three indentations 12 into which an adaptor (such as the turnbull adaptor described below) or other device may be attached. The indentations 12 are arranged at equally spaced intervals around the outer circumference of the exterior section 3.

The interior surface of the exterior section 3 is formed from a three-dimensional porous structure 13 (not shown in detail here), such as porous structure 213 or 313 described below.

All elements of the implant 1 are integral with each other and made from the same material. The implant 1 is formed entirely of titanium.

The implant 1 is manufactured using a laser 3D printing process. After the implants 1 have been printed using the laser 3D printing process, the outer surface of the exterior section 3 is polished to give a smooth finish.

Alternatively, the implant 1 may be moulded and/or made in parts which are subsequently joined together.

FIGS. 6 to 10 show an embodiment of an implant 101 with a larger inner diameter than the implant 1 of FIGS. 1 to 5.

However, like the implant 1 of FIGS. 1 to 5, the implant 101 is also formed of an interior section 102 and an exterior section 103. The interior section 102 is formed of an inner interior section part 104 and an outer interior section part 108.

The inner interior section part 104 has a radially extending part 104a which is terminated by a continuous solid ring 105.

An anchoring flange 106 extends radially outwardly from the inner interior section part 104 and has at its radially outer edge a continuous solid ring 107.

The outer interior section part 108 is formed of a number of rods 109 extending between the inner interior section part 104 and the exterior section 103.

The exterior section 103 has an outer circumferential groove 111 and three indentations 112. The interior surface of the exterior section 103 is formed from a three-dimensional porous structure 113.

Other features of the implant 1 described above apply equally to the implant 101.

Figure 11:
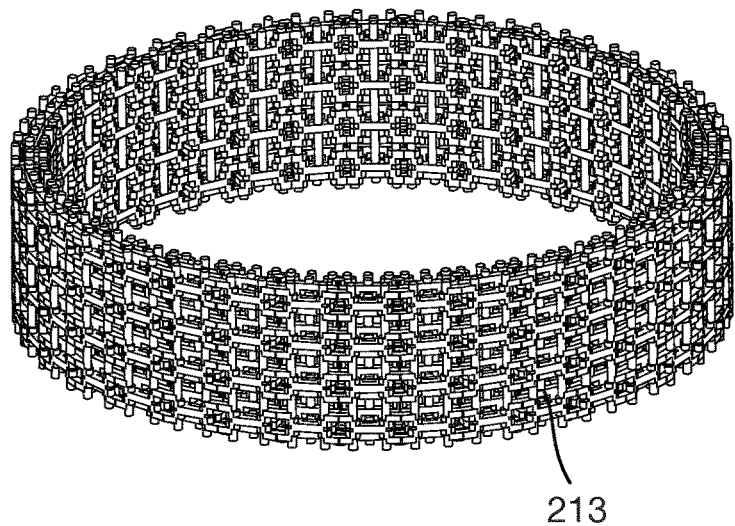
FIG. 11 is a perspective view of a porous structure.
Figure 12:
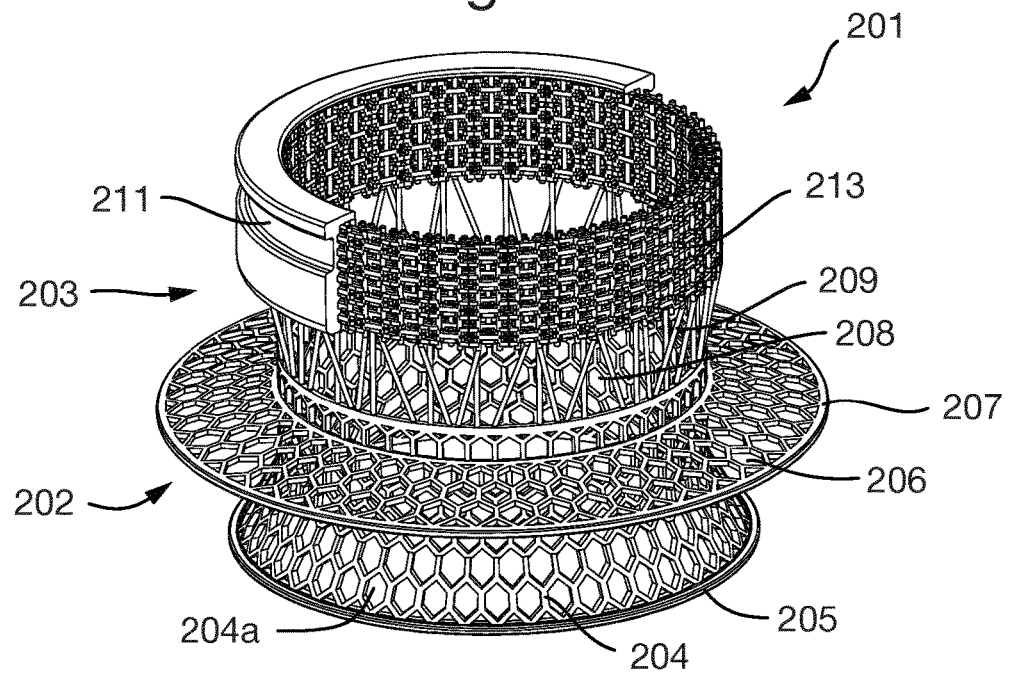
FIG. 12 is a part cut-away perspective view of an implant with the porous structure of FIG. 11.
Figure 13:
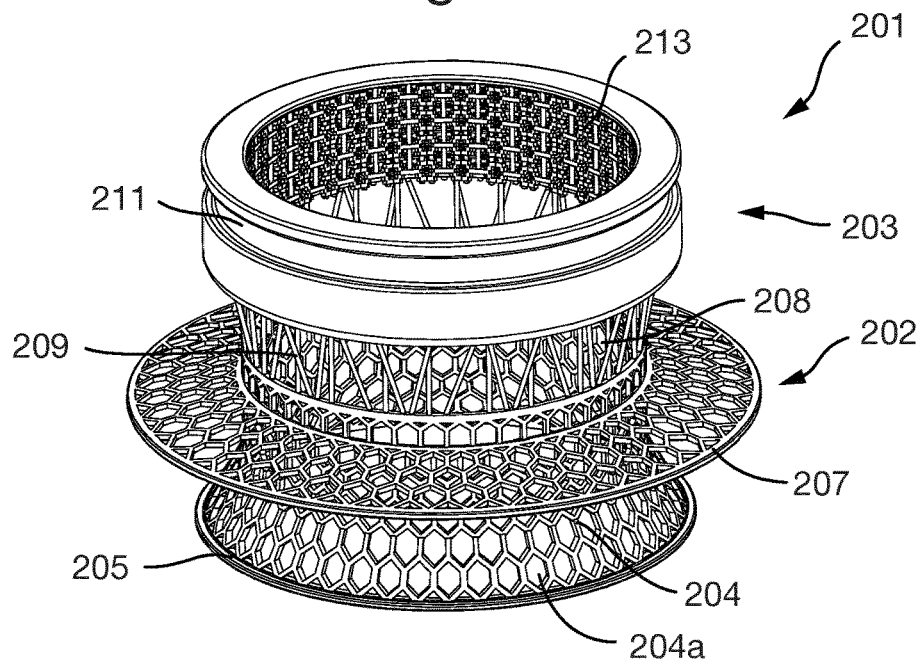
FIG. 13 is a perspective view of an implant with the porous structure of FIG. 11.
Figure 14:
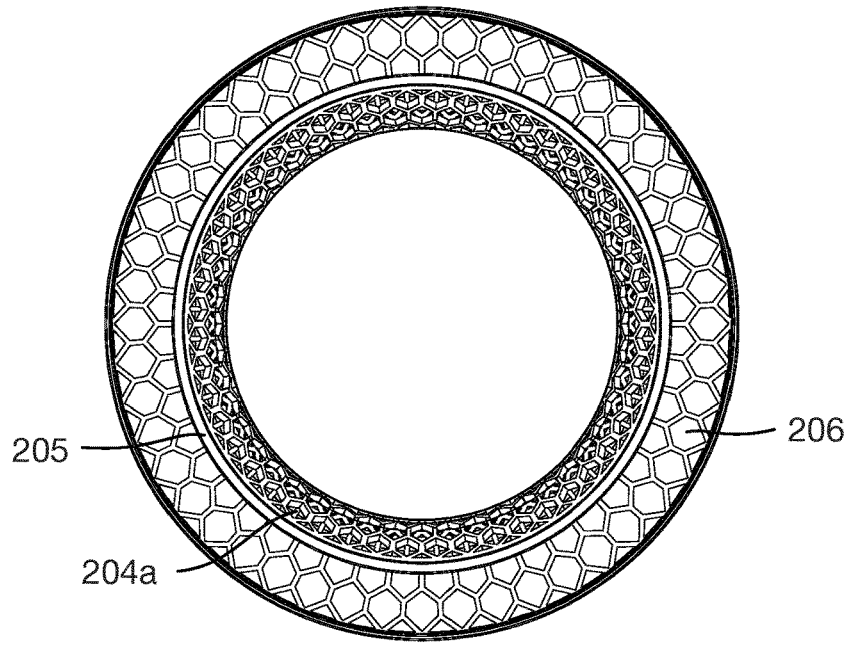
FIG. 14 is a bottom view of the implant of FIG. 13.
Figure 18:
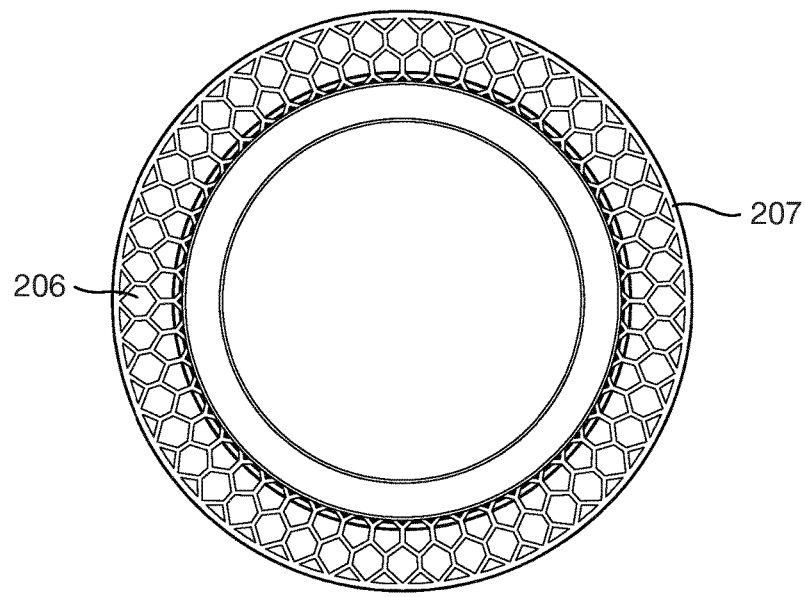
FIG. 18 is a top view of the implant of FIG. 14.
Figure 19:
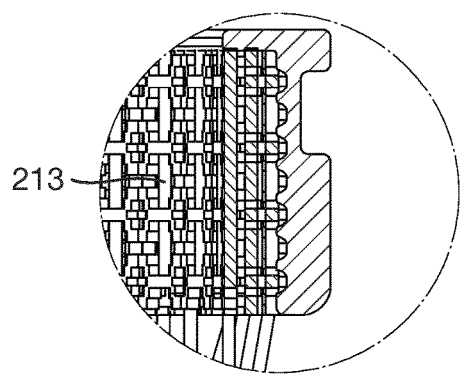
FIG. 19 is shows the area labelled C in FIG. 17 in more detail.
Figure 20:
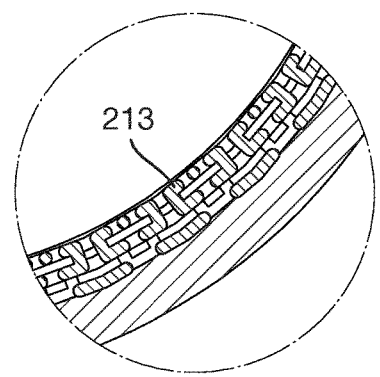
FIG. 20 is the area labelled D in FIG. 16 in more detail.
Figure 21:
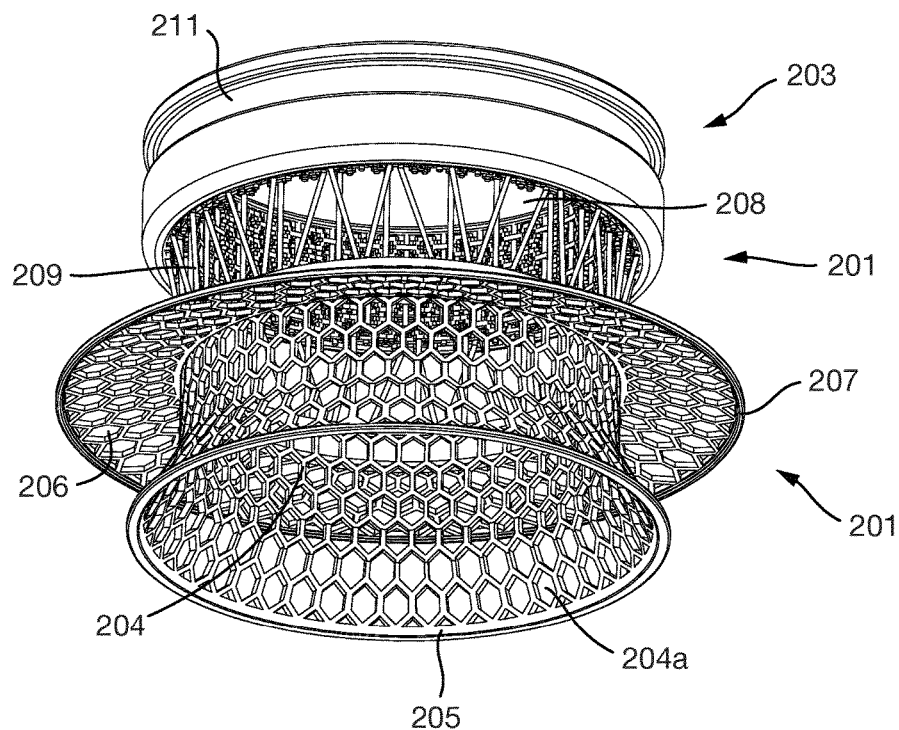
FIG. 21 is another perspective view of the implant of FIG. 13.

FIG. 11 shows a porous structure 213. As shown in FIGS. 12 to 21, the porous structure 213 is in the form of a hollow cylinder or tube located at an inner surface of the exterior section 203.

The implant 201 shown in FIGS. 12 to 21 is generally similar to the implants 1 and 101 described above so its structure will not be described in detail. The only difference to implant 1 is that there are no indentations on the exterior section 203.

The implant 201 is formed of an interior section 202 and an exterior section 203. The interior section 201 is formed of an inner interior section part 204 and an outer interior section part 208.

The inner interior section part 204 has a radially extending part 204a which is terminated by a continuous solid ring 205.

An anchoring flange 206 extends radially outwardly from the inner interior section part 204 and has at its radially outer edge a continuous solid ring 207.

The outer interior section part 208 is formed of a number of rods 209 extending between the inner interior section part 204 and the exterior section 203.

The exterior section 203 has an outer circumferential groove 211 but no indentations. The interior surface of the exterior section 203 is formed from the three-dimensional porous structure 213.

The porous structure 213 is completely permeable; there are no dead ends. Every passage entering the porous structure also has an exit. The maximum thickness of any member forming the porous structure is 300 μm and the maximum diameter of any opening is also 300 μm.

Figure 22:
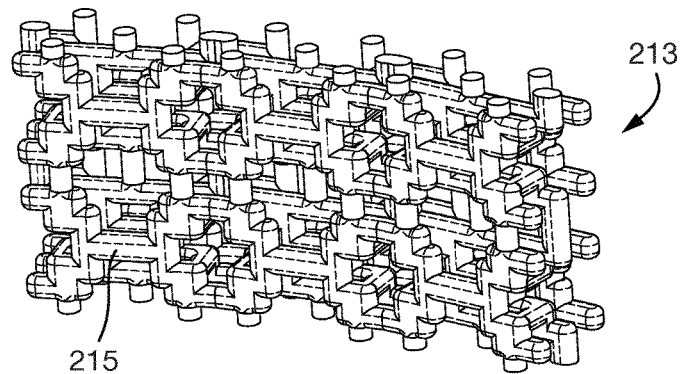
FIG. 22 is a perspective view of part of a porous structure.
Figure 23:
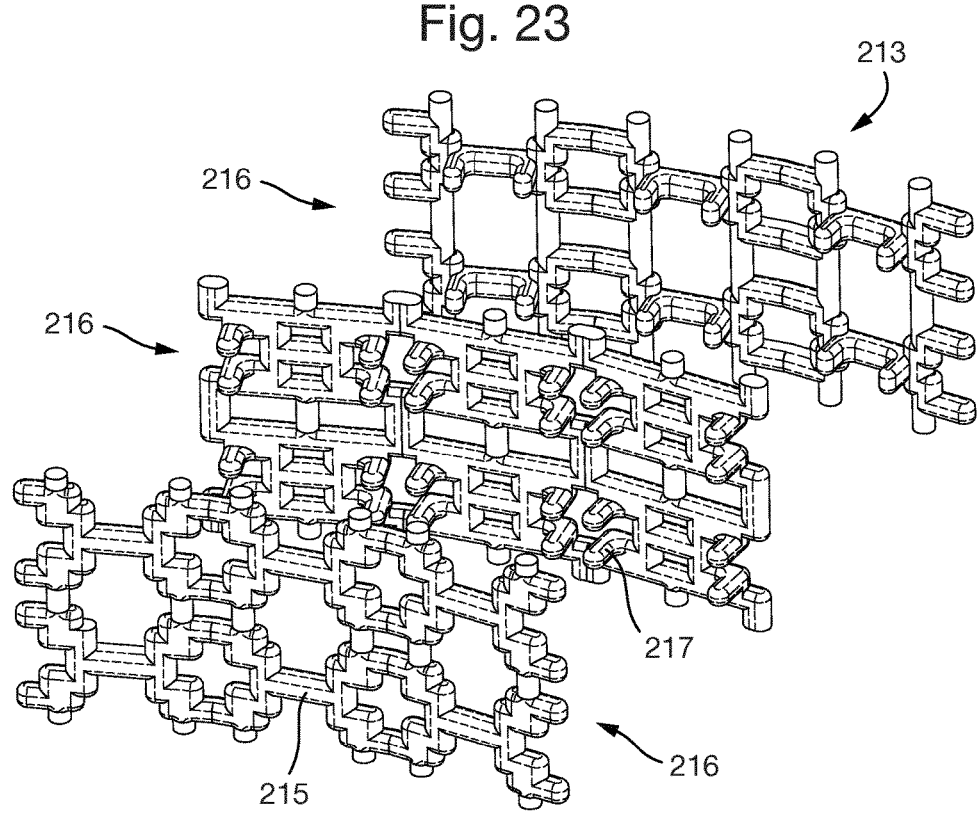
FIG. 23 is an exploded perspective view of the porous structure of FIG. 22.
Figure 24:
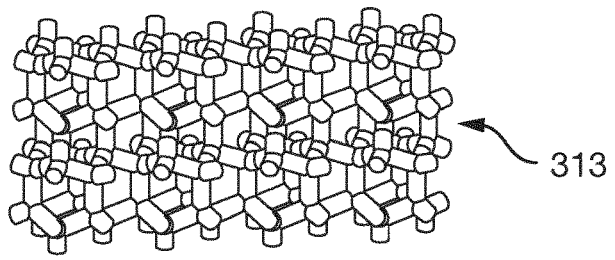
FIG. 24 shows a part of another porous structure.
Figure 25A:
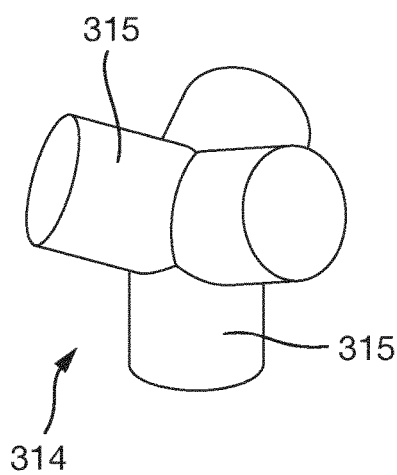
FIGS. 25(a)-(c) show parts of the porous structure of FIG. 24 in more detail.
Figure 25B:
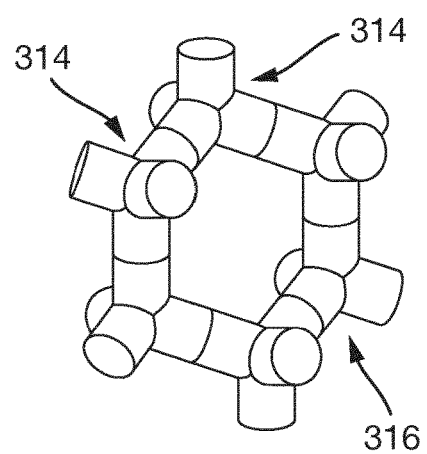
Figure 25C:
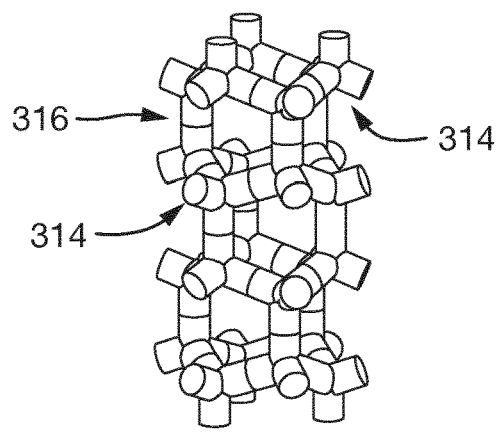
Figure 26A:
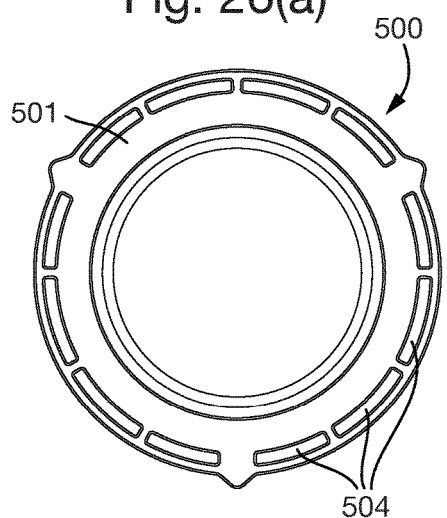
FIGS. 26(a)-(f) show top, bottom, bottom perspective, top perspective, front and side views, respectively, of an embodiment of an adaptor.
Figure 26B:
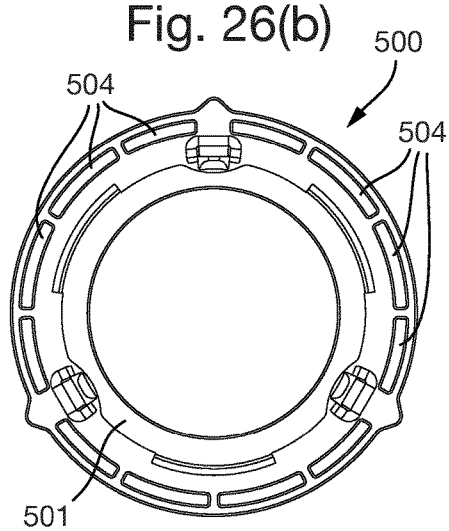
Figure 26C:
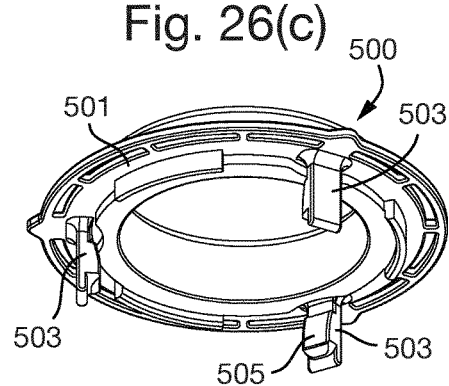
Figure 26D:
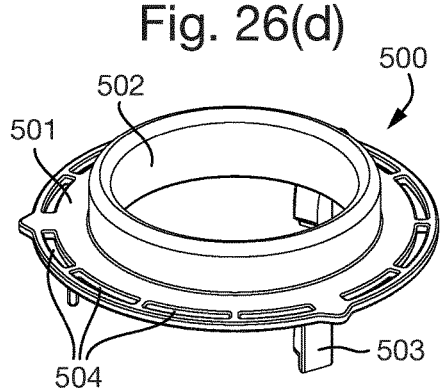
Figure 26E:
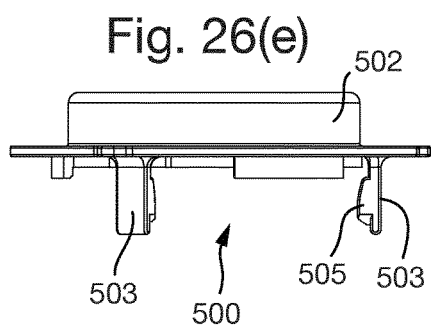
Figure 26F:
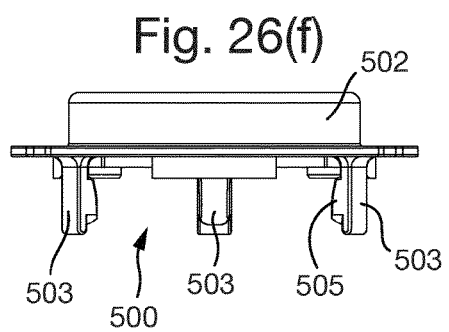

FIGS. 22 and 23 show a part of the porous structure 213 in more detail. It is formed from interconnecting members 215. The members 215 are arranged in layers 216 which are connected by connecting members 217.

In the embodiment shown, the members 215 and 217 form a regular, repeating pattern throughout the porous structure 213. However, in other embodiments, the porous structure has an irregular structure. The apertures in the porous structure have substantially square, rectangular or cross-shaped cross-sections. However, in alternative embodiments, some or all of the apertures are circular or oval.

FIGS. 24 and 25(a)-(c) show an example of another porous structure 313. This porous structure 313 is made up of a number of repeating sub-units 314. Each of the sub-units 314 is formed of four members 315 joined together at a central point of the sub-unit 314 at ends thereof. Six sub-units 314 are joined together to form a generally hexagonal ring or unit 316. The units 316 are then joined together in a regular repeating fashion to form the porous structure 313.

FIGS. 26(a)-(f) show an adaptor 500 for securing a bowel segment outside a patient's body after an ostomy has been performed.

The adaptor 500 is formed of a flattened ring 501 with a short cylindrical part 502 protruding in a first direction from an inner diameter of the ring 501. Three resilient members 503 protrude from the ring 501 in an opposite direction to the cylindrical part 502.

The resilient members 503 are arranged equally spaced around the ring 501 and each member 503 has a protruding part 505 located on a radially inward side of the resilient member 503 and towards an end of the resilient member 503 away from the ring 501.

The ring 501 has a number of slot-shaped apertures 504 (in this case, twelve) arranged around it circumferentially.

As shown in FIGS. 28 to 30, the adaptor 500 can be attached to the exterior section 103 of an implant 101. The protruding parts 505 of the resilient members 503 fit into the indentations 112, thereby attaching the adaptor 500 to the implant 101 and preventing it from moving both rotationally, transversally and longitudinally with respect to the implant 101.

When attached, the adaptor 500 and the implant 101 have a common axis and the adaptor 500 is sized such that it can fit over and be attached to the implant 101. The inner diameter of the adaptor 500 and the exterior section 103 of the implant 101 are the same.

The adaptor 500 is made entirely of plastic and is fabricated in a laser sintering process from medical quality polyamide powder (PA2200).

The adaptor 500 is sterilised by means of autoclaving and is provided sterile. Alternatively, the adaptor 500 may be sterilised by radiation, gas such as ethylene oxide, plasma or other methods.

The adaptor 500 is provided in different sizes, for example two sizes, to fit different sized implants (i.e. implants with different diameters).

The adaptor 500 is intended to be used during the surgical procedure when implanting an implant such as one described above. When attached to the implant 101, the adaptor 500 can receive the bowel segment therethrough and allow the bowel segment to be reverted back over the adaptor 500.

The adaptor 500 can be used to fix the efferent intestine for around 4 to 6 weeks after implantation, in order to provide best possible stress-free healing and in-growth conditions for the ileum during the integration process with the implant.

The adaptor 500 is attached to the exterior section 103 of the implant 101 at the end of the implantation procedure. It is used to secure the efferent intestine with a few sutures, during the first four to six weeks after implantation. Thereafter, the efferent intestine is cut away and the adaptor 500 is removed.

In order to use the adaptor 500, the following steps are performed:

Clip the adaptor 500 onto the exterior section 103 of the implant 101. Turn it lightly to ensure it locks correctly in place.

The efferent end of the intestine is reverted over the adaptor 500 above the implant 101 and secured using sutures through the apertures 504.

Make sure that the groove 111 around the outside of the exterior section 130 is free from tissue so that it can be used for attachment of a stabiliser device (not shown). (A stabiliser device is a device used to secure the implant 101 in place during the healing period by providing support against tilting or vertical movement of the implant 101. It can be attached to the exterior section 103 of the implant 101, for example, and rests on the skin or a skin barrier.)

Anchor the intestine to the peritoneum using sutures.

After a few weeks the intestine should have grown enough into the implant 101 for the adaptor 500 to be removed. The part of the intestine protruding outside the implant 101 will now have started to wizen and is cut away. The adaptor 500 is removed and the intestine will reside permanently just at the top of the implant 101.

In order to remove the adaptor 500, the following steps are performed:

Remove any stoma bag and clean the orifice gently.

Carefully remove the stabiliser device and the stoma skin barrier.

Gently rinse around the implant 101 to remove any intestinal content or liquid.

With a diathermy scalpel, incise the intestine inside of adaptor 500 three millimeters from the top through the entire thickness of the intestine.

If needed, dissect the intestine down to the base of the adaptor 500 with a forceps. Do not to go beyond the base of the adaptor 500 as this could cause harm to the tissue in-growth into the implant cylinder, resulting in leakage.

With a pointed object, carefully lift the resilient members 503 out of the indentations 112 in the exterior section 103 and remove the adaptor 500 slowly.

With dissection scissors, trim any excess tissue that remains above the exterior section 103 of the implant 101. If catheterization is needed, do not to touch the inside (interior diameter) of the implant 101.

Put a new skin barrier, stabiliser and stoma bag in place.

What is claimed is:

1. An implant comprising a tubular interior section for implantation into a patient and an exterior section connected to the interior section, wherein the exterior section includes as a separate element a surface comprising a rigid three-dimensional porous structure in contact with the exterior section at an inner circumference thereof, wherein the exterior section comprises a solid body, and wherein the porous structure is permeable, porous in multiple directions and is configured and dimensioned to fit within an inner surface of the solid body with no gap between the porous structure and the exterior section.

2. An implant comprising a tubular interior section for implantation into a patient and an exterior section connected to the interior section, wherein the exterior section includes as a separate element a surface comprising a rigid three-dimensional porous structure that is porous in multiple directions at an inner circumference thereof, wherein: the exterior section comprises a solid body, wherein the porous structure is permeable and is configured and dimensioned to fit within an inner surface of the solid body with no gap between the porous structure and the exterior section; and wherein:

the porous structure is integral with the exterior section; or the porous structure is connected to the exterior section at least at first and second end regions thereof; or the porous structure extends to within 1 mm, 2 mm or 3 mm of an exterior end of the exterior section; or the porous structure is arranged around the entire inner circumference of the exterior section.

3. The implant of claim 1, which is a percutaneous ostomy implant for implantation into the abdominal wall of a patient.

4. The implant of claim 1, wherein the exterior section is ring-shaped.

5. The implant of claim 1, wherein the porous structure is made from titanium.

6. The implant of claim 1, wherein the porous structure has a thickness of at least 0.5 mm.

7. The implant of claim 1, wherein the porous structure is completely permeable and has no dead ends.

8. The implant of claim 1, wherein at least 80%, at least 85%, at least 90%, at least 95%, or at least 97% of the openings into the porous structure have a corresponding exit, or each passage entering the porous structure has an exit.

9. The implant of claim 1, wherein the porous structure is formed of interconnecting members, each member forming the porous structure having a thickness that is less than or equal to 500 µm, less than or equal to 450 µm, less than or equal to 400 µm, less than or equal to 350 µm, or less than or equal to 300 µm.

10. The implant of claim 1, wherein each opening in the porous structure has a maximum diameter of 500 µm, 450 µm, 400 µm, 350 µm, or 300 µm.

11. The implant of claim 1, wherein the three-dimensional porous structure comprises a plurality of interconnecting members, and the interconnecting members form a regular, repeating pattern throughout the porous structure or an irregular structure, and are optionally arranged concentrically.

12. The implant of claim 1, wherein the tubular interior section has first and second ends; the exterior section has first and second ends and a body for attachment to an adaptor or other removable device, with the second end of the exterior section connected to the first end of the interior section, with the exterior section having inner and outer surfaces extending between the first and second ends.

13. The implant of claim 1, further comprising an anchoring flange extending radially outwardly from the interior section, optionally in the form of a mesh.

14. An implant as claimed in claim 1, in combination with a mating lid, bag and/or evacuation device.

15. A kit comprising an implant and an adaptor for securing a bowel segment outside a patient's body after an ostomy has been performed, wherein the implant is as claimed in claim 1, and the adaptor optionally comprising attachment means for attaching the adaptor to the implant; and securing means to which a bowel segment may be attached.

16. The kit of claim 15, wherein a tubular body of the adaptor has first and second ends, and is configured and dimensioned to receive an exterior portion of an implant therein; with the adaptor further comprising a radially extending part connected to the body that includes the securing means for receiving a bowel segment for attachment thereto.

17. An implant comprising a tubular interior section for implantation into a patient and an exterior section connected to the interior section, wherein the exterior section comprises a solid body, wherein the exterior section includes as a separate element a surface comprising a rigid three-dimensional porous structure that is permeable and porous in multiple directions and is configured and dimensioned to fit within an inner surface of the solid body such that there is no open gap between the porous structure and the exterior section; wherein the porous structure is integral with the exterior section or is connected to the exterior section at least at first and second end regions thereof; and extends to within 1 mm, 2 mm or 3 mm of an exterior end of the exterior section or around the entire inner circumference of the exterior section.

18. The implant of claim 17 wherein the rigid three-dimensional porous structure extends around the inner circumference of the exterior section to within 3 mm of its exterior end thereof.

\* \* \* \* \*